United States Patent
Akhavan-Tafti et al.

(10) Patent No.: US 6,897,036 B2
(45) Date of Patent: May 24, 2005

(54) FLUORESCENT DETECTION OF PEROXIDASE ENZYMES

(75) Inventors: Hashem Akhavan-Tafti, Howell, MI (US); Renuka de Silva, Northville, MI (US); Mark Sandison, Dearborn, MI (US); Richard Handley, Canton, MI (US)

(73) Assignee: Lumigen, Inc., Southfield, MI (US)

( * ) Notice: Subject to any disclaimer, the term of this patent is extended or adjusted under 35 U.S.C. 154(b) by 251 days.

(21) Appl. No.: 10/163,750

(22) Filed: Jun. 6, 2002

(65) Prior Publication Data

US 2003/0232405 A1 Dec. 18, 2003

(51) Int. Cl.[7] .............................. C12Q 1/28; C12Q 1/00; G01N 33/53
(52) U.S. Cl. .............................. 435/28; 435/968; 435/4
(58) Field of Search ............................. 435/28, 968, 4

(56) References Cited

U.S. PATENT DOCUMENTS

| | | | | |
|---|---|---|---|---|
| 4,521,511 A | | 6/1985 | Stout ........................... 435/28 |
| 5,171,668 A | | 12/1992 | Sugiyama ..................... 435/28 |
| 5,206,149 A | | 4/1993 | Oyama et al. ................. 435/28 |
| 5,491,072 A | * | 2/1996 | Akhavan-Tafti et al. ...... 435/28 |
| 5,512,451 A | | 4/1996 | Kricka et al. ................. 435/28 |
| 5,523,212 A | | 6/1996 | Akhavan-Tafti ............. 435/28 |
| 5,545,834 A | | 8/1996 | Singh ........................... 544/6 |
| 5,593,845 A | * | 1/1997 | Akhavan-Tafti et al. ..... 435/7.9 |
| 5,670,644 A | * | 9/1997 | Akhavan-Tafti et al. .... 546/103 |
| 5,723,295 A | * | 3/1998 | Akhavan-Tafti et al. ....... 435/6 |
| 5,750,698 A | * | 5/1998 | Akhavan-Tafti et al. .... 546/102 |
| 6,030,803 A | | 2/2000 | Jacquemijns et al. ......... 435/28 |
| 6,040,150 A | | 3/2000 | Savage ......................... 435/4 |
| 6,045,727 A | * | 4/2000 | Akhavan-Tafti et al. .... 252/700 |
| 6,090,571 A | * | 7/2000 | Akhavan-Tafti et al. ...... 435/21 |
| 6,162,931 A | | 12/2000 | Gee ............................. 549/223 |
| 6,296,787 B1 | * | 10/2001 | Akhavan-Tafti et al. .... 252/700 |
| 6,410,732 B2 | * | 6/2002 | Akhavan-Tafti et al. .... 546/102 |

FOREIGN PATENT DOCUMENTS

WO    WO 99/01768    1/1999

OTHER PUBLICATIONS

L.J. Kricka and G.H.G Thorpe, in Luminescene Immunoassay and Molecular Applications, K. VanDyke and R. VanDyke, eds., CRC Press, Boca Raton, 1990, pp. 77–98.
Zaitsu and Ohkura, Anal. Biochem., 109, 109–113 (1980).
Y. Li, et al., Anal. Chim. Acta, (340), 159–168, (1997).
Li, et al., Microchem. J., 53(4), 428–436 (1996).
M. Kawaguchi, et al., Bioluminescene and Chemiluminescence Perspectives for the 21st Century, A. Koda et al., Eds., Wiley & Sons, Chichester, pp 508–511, (1999).
D.O. Shah and V. A. Salbilla, Proceedings of the 11th International Symposium on Bioluminescence and Chemiluminescence, J. F. Case et al., Eds., Wiley & Sons, Chichester, pp 235–238, (2001).
Y.–X. Ci, et al., Mikrochem. J., 52, 257–62 (1995).
Amersham Pharmacia Biotech Application Note: Fluorescent Western Blotting. Available at http://www.mdyn.com/app_notes/appnotes/AN68/APP%2068.pdf.
M. Ii, H. Yoshida, Y. Aramaki, H. Masuya, T. Hada, M. Terada, M. Hatanaka, Y. Ichimori, Biochem. Biophys. Res. Comm., 193(2), 540–5 (1993).

* cited by examiner

Primary Examiner—Louise N. Leary
(74) Attorney, Agent, or Firm—Richard S. Handley (57) ABSTRACT

Methods of producing fluorescence from fluorogenic substrates reactive with a peroxidase enzyme are disclosed. Use of the methods in assays for peroxidase enzymes, peroxidase-labeled analytes are provided. Fluorogenic compounds, compositions and kits for reaction with peroxidase enzymes are described. Two modes of producing fluorescent compounds are described.

16 Claims, 5 Drawing Sheets

FLUORESCENT DETECTION OF PEROXIDASE ENZYMES

FIELD OF THE INVENTION

This invention relates to fluorogenic compounds and methods of using them in detecting peroxidase enzymes. The invention also relates to the use of these methods to detect analytes linked to a peroxidase or to a member of a specific binding pair which has a specific affinity to a peroxidase-labeled specific binding partner.

BACKGROUND OF THE INVENTION

Peroxidase enzymes such as horseradish peroxidase (HRP) are frequently used as markers or labels in enzyme-linked assays for biological molecules and other analytes of interest such as drugs, hormones, steroids and cancer markers. Detection of these enzymes can be achieved by the use of substrates which produce a detectable product. Chromogenic substrates such as o-phenylenediamine, ABTS or tetramethylbenzidine (TMB) produce a colored reaction product, fluorogenic substrates produce a fluorescent product, while chemiluminescent substrates produce light as the detectable product. Each of these methods can offer a safe, convenient and sensitive means to provide a quantitative measure of the amount of enzyme in a sample or of the amount of an enzyme-labeled analyte or labeled specific binding partner for an analyte.

a. Chemiluminescent Peroxidase Substrates

Applicant's U.S. Pat. Nos. 5,491,072, 5,523,212 and 5,593,845 disclose chemiluminescent N-alkylacridancarboxylic acid esters, thioesters and sulfonimides which produce light upon reaction with a peroxide and a peroxidase for use in detecting peroxidases and in assays. U.S. Pat. No. 5,545,834 describes the chemiluminescent reaction of spiroacridan compounds with hydrogen peroxide. The reaction is enhanced by the addition of horseradish peroxidase (HRP).

Various compounds of biological origin, collectively termed luciferins, are oxidized by a peroxidase (summarized in L. J Kricka and G. H. G. Thorpe, in Luminescence Immunoassay and Molecular Applications, K. Van Dyke and R. Van Dyke, eds., CRC Press, Boca Raton, 1990, pp. 77–98). In some instances, hydrogen peroxide is not utilized in which case the enzyme is functioning as an oxidase.

b. Fluorescent Peroxidase Substrates

U.S. Pat. No. 6,040,150 discloses an improved method of generating a fluorescent reporter compound from reaction of a fluorogenic substrate with a peroxidase. The method comprises using a phenolic compound as substrate including 3-(4-hydroxyphenyl)-propionic acid. Other phenolic fluorogenic substrates are disclosed in Zaitsu and Ohkura, Anal. Biochem., 109, 109–113 (1980) and include 2-(4-hydroxyphenyl)acetic acid, homovanillic acid and tyramine (Y. Li, et al., Anal. Chim. Acta, (340), 159–168, (1997)). Other art-known fluorogenic peroxidase substrates include o-phenylenediamine and N,N'-dicyanomethyl-o-phenylenediamine (Li, et al., Microchem. J., 53(4), 428–436 (1996)), amide and carbamate derivatives of p-aminophenol (M. Kawaguchi, et al., Bioluminescence and Chemiluminescence Perspectives for the 21st Century, A. Roda et al., Eds., Wiley & Sons, Chichester, pp 508–511, (1999)), 3,4-dihydro-2(1H)-quinoxalone and related derivatives (Li, et al., Anal. Chim. Acta, 340(1–3), 159–168 (1997)), reduced forms of fluorescein, rhodamine and other xanthine dyes and fluorinated derivatives of the latter (U.S. Pat. No. 6,162,931 and PCT Patent Publication WO99/01768).

c. Fluorescent Detection of Acridinium Labels

Acridinium esters and amides are known in the art of chemiluminescence. These compounds are generally used to label a substance to be detected in an assay. Detection by chemiluminescence comprises reaction of the label with a strongly alkaline hydrogen peroxide solution. A fluorometric assay of acridinium labeled compounds has also been described in which these same chemiluminescent compounds are measured by their inherent fluorescence (D. O. Shah and V. A. Salbilla, Proceedings of the 11th International Symposium on Bioluminescence and Chemiluminescence, J. F. Case et al., Eds., Wiley & Sons, Chichester, pp 235–238, (2001)).

IN THE DRAWINGS

FIG. 3 is a graph showing the linearity of detection of HRP using fluorogenic substrates performed according to the methods of the present invention. Solutions containing 0.05 mM substrate 1 or 4, 0.1 mM 4-phenylphenol, 0.5 mM urea peroxide, 1 mM EDTA, 0.025% TWEEN 20 in 10 mM acetate buffer, pH 5 and a solution of 0.05 mM substrate 2, 0.1 mM 4-phenylphenol, 0.5 mM urea peroxide, 1 mM EDTA, 0.025% TWEEN 20 in 10 mM in 10 mM tris, pH 8 were reacted with the indicated quantities of HRP. After a reaction period of 15–20 min, fluorescence intensity was measured at the maximum. The term Intensity-Background refers to the fluorescence intensity in relative light units in the presence of HRP corrected for background fluorescence (B) in the absence of HRP. In this manner, less than 1 amol of HRP was detectable.

OBJECTS

It is therefore an object of the present invention to provide a method for producing a fluorescent compound comprising reacting a fluorogenic substrate for a peroxidase enzyme with a peroxidase enzyme. Another object is to provide a method of detecting a peroxidase enzyme by reacting a fluorogenic substrate with the peroxidase to produce a fluorescent reaction product and then detecting the fluorescent reaction product. Another object is to provide a method of detecting an analyte in an assay procedure in which a labeled analyte or labeled analyte-binding compound is labeled with a peroxidase enzyme and the peroxidase enzyme is reacted with a fluorogenic peroxidase substrate to produce a fluorescent reaction product.

DESCRIPTION OF THE PREFERRED EMBODIMENTS

The present invention relates to fluorogenic compounds for producing fluorescence upon reaction with a peroxidase enzyme and a peroxide. Compounds useful in the practice of the methods of the present invention will fall into one of two categories depending on the mode of use.

One group of compounds of the present invention has the formula I:

I wherein $R^1$ is a group selected to be inert to attack by peroxide and containing from 1 to 20 atoms selected from C, H, N, O, S, P, Si and halogens, $R^2$ is selected from alkyl, substituted alkyl, aryl substituted aryl, aralkyl and substituted aralkyl groups, and $R^3$ to $R^{10}$ are each groups containing from 1 to 20 atoms selected from C, H, N, O, S, P, Si and halogens. Groups $R^1$ which are not inert to attack by peroxide in the sense intended herein include aryl esters (—COOAr), alkyl esters (—COOR) wherein the alkyl group R is substituted with electron-withdrawing groups such as halogen, cyano and nitro since these substituents increase the leaving group ability of the —OR group, alkyl and aryl thioesters (—COSR, COSAr), sulfonimides (—CO(NR)SO$_2$R'), —C(=O)X wherein X is a halogen and the cyano group. The group $R^1$ is preferably selected from alkyl, substituted alkyl, alkenyl, substituted alkenyl, alkynyl, substituted alkynyl, alkoxy, alkylthio, aryl, substituted aryl, aralkyl, substituted aralkyl, carboxylic acid, carboxylate salt, carboxamide, alkyl carboxyl ester, carboxyl hydrazide groups, keto groups, —CHO, amino, alkylamino, arylamino, and a hydrogen atom. The groups $R^3$ to $R^{10}$ are preferably selected independently from hydrogen, alkyl, alkoxy, alkylthio, amino, alkylamino, arylamino, aryl, alkenyl, alkynyl, halogen, hydroxy, mercapto, sulfonate, sulfate, and phosphate.

When a group is termed substituted it is intended that one or more of the hydrogen atoms on the carbon skeleton of the group in question is replaced by a different atom or group. Groups commonly understood to be included within this usage include halogens, hydroxy, alkoxy, aryloxy, trialkylsilyloxy, amino, alkylamino, arylamino, alkylthio, arylthio, mercapto, nitro, sulfonate, sulfate, phosphate, phosphonate, cyano, carboxylate, carboxyl ester, carboxamido, and carboxaldehyde.

In one embodiment the fluorogenic compound of formula I will contain hydrogen atoms for each of the substituents $R^3$ to $R^{10}$. Compounds in this group have the formula shown below where $R^1$ and $R^2$ are as defined above.

In another embodiment the fluorogenic compound of formula I contains at least one group which imparts water solubility. Preferred groups include carboxylate, sulfonate, sulfate, phosphate, ammonium and phosphonium groups. Water-solubilizing groups can be substituted at any of the $R^1$ position, the $R^2$ position or the positions $R^3$–$R^{10}$.

In another embodiment the fluorogenic compound of formula I can comprise additional ring groups by joining two adjacent positions on the acridan ring with a linking chain. The additional ring will comprise a four to seven-membered ring, preferably a five or six-membered ring. The ring can comprise saturated atoms or additional unsaturation such as a double bond or a benzenoid ring. Exemplary structures shown for purposes of illustration are depicted below. The additional rings can contain further substituents as defined above.

In another embodiment the fluorogenic compound of formula I is selected from the following compounds 1–11.

1

2

3

4

5

6

7

8

9

10

11

12

13

In another embodiment the fluorogenic substrates have formula II

II wherein R¹ is a group which contains within it a leaving group which can be displaced by peroxide acting as a nucleophile and is selected from aryl esters (—COOAr), substituted alkyl esters (—COOR) wherein the alkyl group R is substituted with electron-withdrawing groups such as halogen, cyano and nitro which increase the leaving group ability of the —OR group, thioesters (—COSR, COSAr), sulfonimides (—CO(NR)SO₂R'), —C(=O)X wherein X is a halogen and the cyano group, and wherein R² is selected from alkyl, substituted alkyl, aryl substituted aryl, aralkyl and substituted aralkyl groups, and R³ to R¹⁰ are each groups containing from 1 to 20 atoms selected from C, H, N, O, S, P, Si and halogens wherein at least one of R³ or R¹⁰ is a group other than H which sterically prevents a chemiluminescent reaction producing an acridone product under conditions compatible with peroxidase activity. The groups R³ to R¹⁰ are preferably selected independently from hydrogen, alkyl, alkoxy, alkylthio, amino, alkylamino, arylamino, aryl, alkenyl, alkynyl, halogen, hydroxy, mercapto, sulfonate, sulfate, and phosphate. Preferably at least one of R³ or R¹⁰ is a halogen, an alkyl or an alkoxy group. Pairs of adjacent substituents in formula II can be joined together as a ring in the same manner as defined above for formula I. Compounds of formula II form a stable acridinium product under the conditions of the enzymatic reaction with peroxidase but are sterically prevented from undergoing the subsequent chemiluminescent reaction under conditions compatible with peroxidase activity. Exemplary compounds falling into this group are described in U.S. Pat. Nos. 5,670,644 and 5,723,295 which are fully incorporated herein by reference and include aryl and alkyl esters, thioesters and sulfonamides.

Another group of fluorogenic compounds will have the formula III below.

III wherein R¹ is a group which contains within it a leaving group which can be displaced by peroxide acting as a nucleophile and is selected from aryl esters (—COOAr), substituted alkyl esters (—COOR) wherein the alkyl group R is substituted with electron-withdrawing groups such as halogen, cyano and nitro which increase the leaving group ability of the —OR group, thioesters (—COSR, COSAr), sulfonimides (—CO(NR)SO₂R'), —C(=O)X wherein X is a halogen and the cyano group, and wherein R² is selected from alkyl, substituted alkyl, aryl substituted aryl, aralkyl and substituted aralkyl groups, and R³ to R¹⁰ are each groups containing from 1 to 20 atoms selected from C, H, N, O, S, P, Si and halogens with the proviso that the compound of formula I does not include the compound designated as compound 12 above designated 2,3,6-trifluorophenyl N-methylacridan-9-carboxylate. The groups R³ to R¹⁰ are preferably selected independently from hydrogen, alkyl, alkoxy, alkylthio, amino, alkylamino, arylamino, aryl, alkenyl, alkynyl, halogen, hydroxy, mercapto, sulfonate, sulfate, and phosphate. Pairs of adjacent substituents in formula III can be joined together as a ring in the same manner as defined above for formula I and II.

In another embodiment the present invention relates to a method for producing fluorescence which comprise reacting a compound of formula I, II or III with a peroxidase enzyme and optionally a peroxide to produce a fluorescent product. The fluorescent product thus formed is irradiated at a suitable wavelength of light to cause the fluorescent product to emit fluorescence. Wavelengths of light suitable for excitation of fluorescence are determined empirically using means well known to the skilled artisan such as by recording an absorption spectrum or a fluorescence excitation spectrum. It may be advantageous to select a wavelength or range of wavelengths at which excitation is maximal but it is not necessary to do so. Excitation wavelength may also be selected based on the characteristics of the light source, particularly when monochromatic laser light sources are used.

The present methods encompass two different modes of reaction. In one embodiment the fluorogenic substrate of formula I or II is converted to the ring oxidized acridinium reaction product which is fluorescent. This product accumulates under the enzymatic reaction conditions as it undergoes no further reaction, even in the presence of excess peroxide.

Scheme 1

Fluorogenic Substrate

Fluorescent Product

This mode of reaction operates when the fluorogenic substrate is of formula I or II which does not allow a rapid and irreversible chemiluminescent reaction to occur by attack of peroxide at the 9-position as shown in Scheme 2.

Scheme 2

Substituents at the 9-position which promote the subsequent irreversible consumption of the fluorescent acridinium reaction product to produce chemiluminescence and the acridone product comprise compounds of formula III. Exemplary compounds are listed in Applicants' U.S. Pat. Nos. 5,491,072, 5,523,212 and 5,593,845 and in U.S. Pat. No. 6,030,803 include aryl esters (—COOAr), alkyl esters (—COOR) wherein the alkyl group R is substituted with groups such as halogen, cyano and nitro which increase the leaving group ability of the —OR group, thioesters (—COSR, COSAr), sulfonimides (—CO(NR)SO$_2$R') and the cyano group.

A second mode of reaction is made possible when the fluorogenic substrate is of formula III and which allows a rapid and irreversible chemiluminescent reaction to occur following attack of peroxide at the 9-position. Reaction of such substrates proceeds to form the ring oxidized acridinium compound as shown in Scheme 1. The presence of the 9-position substituent which contains a good leaving group and the lack of a sterically hindering group facilitates a further chemiluminescent reaction of the acridinium compound as depicted above in Scheme 2. In this mode the fluorescent acridinium compound is more properly viewed as an intermediate since it does not permanently accumulate. The final reaction product of this reaction sequence is acridone which itself is fluorescent, emitting maximally at 430–450 nm. A chemiluminescent compound which reacts in this manner serves as the basis for a commercial chemifluorescent detection system (ECL Plus Chemifluorescent System, Amersham Pharmacia Biotech). The peroxidase substrate used in this product is the chemiluminescent acridan 2,3,6-trifluorophenyl N-methyl-acridan-9-carboxylate.

What does not appear to have been recognized is that a measurable concentration of the fluorescent acridinium ester intermediate is formed during the course of the reaction along with the acridone product and that the fluorescence spectra of the two species differ from and overlap one another. Applicants have discovered that this behavior is in fact observed in a number of chemiluminescent substrates all of which operate according to the second mode of reaction as described above. Those substrates bearing substituents at the 9-position which enable them to undergo subsequent chemiluminescent transformation of the intermediate acridinium compound can be detected as fluorescent substrates by detecting the fluorescence of either the acridinium compound or the acridone product. Applicants have further discovered that the relative amounts of the two species formed changes over the course of a reaction and also varies depending on the quantity of enzyme used.

This fluorescent behavior differs fundamentally from the fluorescence produced by the first mode of reaction in two aspects. The acridinium compounds are excited at shorter wavelengths than the acridone final product and they emit at longer wavelengths than the acridone product, typically about 500–520 nm. Stated another way, the Stokes shift of the acridinium intermediates is approximately 150 nm while that of the acridone is less than 50 nm. More importantly, detection of the fluorescence of the transiently formed acridinium compounds during the reaction of the group of acridan fluorogenic substrates which are capable of generating chemiluminescence exhibits a completely different time course. In detecting the end product of a reaction, signal gradually rises to a maximum level and remains constant. Detecting an intermediate produces a detectable signal which initially rises for some period and then decays.

Substrates which undergo the first mode of reaction do so over a wide range of pH and peroxide concentrations. The pH is limited only by the operative range of the enzyme. Peroxidase enzymes are known to function over the pH range of about 4–10. Substrates which undergo the second mode of reaction do so in a manner which is influenced by pH and peroxide concentration. High peroxide concentration and pH values above about 7 promote the consumption of the intermediate acridinium compound.

The peroxide component is described as being an optional component of the present reaction even though peroxide is the primary substrate of peroxidase enzymes. Peroxide is generally described as being a necessary reaction component in other peroxidase-catalyzed fluorescent reactions known in the art and listed above in the background section. Applicants have found however that under conditions of relatively high enzyme concentration that peroxide is not needed in the reaction to convert the fluorogenic substrate to the fluorescent product.

In a further embodiment the present invention relates to the use of the method of producing a fluorescent product by the action of a peroxidase on a fluorogenic substrate in a method of detecting the peroxidase enzyme or a conjugate of a peroxidase enzyme with a biological molecule. The peroxidase or peroxidase conjugate is reacted with the fluorogenic substrate to produce the fluorescent product and the fluorescent product is irradiated with light to induce the emission of fluorescence. The fluorescence is detected and the amount or intensity of fluorescence is related to the amount of the peroxidase.

In a further embodiment the present invention relates to the use of the method of detecting a peroxidase conjugate by fluorescence as just described in an assay of an analyte in a procedure wherein the peroxidase enzyme is linked to the analyte or a binding partner which specifically binds the analyte. The means of linking the peroxidase to either the analyte or the analyte-binding partner includes direct covalent attachment and indirect means including hapten/antihapten binding pairs. For example, a biotin-labeled analyte can be specifically bound or captured by a conjugate of peroxidase coupled to streptavidin or an anti-biotin antibody. In such assay methods the amount of fluorescent product formed is related to the amount of the peroxidase as described above and the amount of the peroxidase is related to the amount of analyte. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications.

In a further embodiment the present invention also relates to the use of these methods for detecting a peroxide. Over certain limiting ranges of peroxidase enzyme concentration, which can be determined experimentally, the rate of reaction of a fixed amount of peroxidase and a fixed concentration of fluorogenic substrate is proportional to the amount of peroxide available for reaction. During a specified time interval, differing amounts of peroxide will give rise to different amounts of fluorescent product. The range of peroxide concentration which can be accurately measured can be easily determined by analysis of serial dilutions of a peroxide standard.

In a further embodiment the present invention also relates to the use of these methods for detecting an enzyme which produces peroxide such as an oxidase enzyme or a dehydrogenase enzyme. It is well known that various enzymes in the class of oxidase enzymes produce hydrogen peroxide as a byproduct of the reaction which oxidizes its substrate. Known oxidase enzymes include galactose oxidase, glucose oxidase, cholesterol oxidase, amine oxidase, various amino acid oxidases, polyphenol oxidase, xanthine oxidase, uricase, alcohol dehydrogenase, lactate dehydrogenase, malate dehydrogenase, glyceraldehyde-3-phosphate dehydrogenase, glycerol dehydrogenase, and glucose-6-phosphate dehydrogenase. In practice, the oxidase enzyme is reacted with a substrate for the oxidase enzyme to produce hydrogen peroxide. After a suitable time period, the accumulated hydrogen peroxide is reacted with a peroxidase and a fluorogenic substrate of formula I to produce the fluorescent product which is detected by its fluorescence as described above. The oxidase and peroxidase reactions can be performed concurrently or consecutively.

In another embodiment of the present invention, the fluorogenic compound is advantageously provided in a reagent composition for reaction with a peroxidase enzyme. The reagent composition comprises an aqueous solution containing a compound of formula I, II or III and a peroxide compound. The formulation can further comprise an enhancer substance which can be a phenolic compound to enhance the reactivity of the peroxidase. Additional optional components include a surfactant, a chelating agent which prevents activating the peroxide compound prior to reaction with the peroxidase and an organic solvent to aid in solubilizing the substrate.

The reagents and materials used in the practice of the present invention can be packaged into kits for detecting any of an analyte, a hydrolytic enzyme or a hydrolytic enzyme conjugate in an assay procedure by a detection reaction which produces a fluorescent product. Kits useful for practicing the present invention in any of its embodiments will comprise in one or more containers:

a) a fluorogenic compound as described above in a buffer solution;

b) a peroxide if the analyte to be detected is not the peroxide or a reagent which generates peroxide;

c) a peroxidase enzyme, if the analyte to be detected is not the peroxidase or a conjugate of a peroxidase with the analyte or a conjugate of a peroxidase with a reagent which forms a specific binding pair with the analyte;

d) optionally, an enhancer compound;

e) optionally, a surfactant;

f) and optionally, a chelating agent.

Kit components may be packaged separately or in various combinations as will be apparent on consideration of the various modes of carrying out reactions of the present invention detailed below.

The peroxide component is any peroxide or alkyl hydroperoxide capable of reacting with the peroxidase. Preferred peroxides include hydrogen peroxide, urea peroxide, and perborate salts.

The peroxidase which can undergo the fluorogenic reaction include lactoperoxidase, microperoxidase, myeloperoxidase, haloperoxidase, e.g. vanadium bromoperoxidase, horseradish peroxidase, fungal peroxidases such as lignin peroxidase and peroxidase from Arthromyces ramosus and Mn-dependent peroxidase produced in white rot fungi, and soybean peroxidase. Other peroxidase mimetic compounds which are not enzymes but possess peroxidase-like activity including iron complexes such as heme, hemin and other related iron-porphyrin complexes and Mn-TPPS$_4$ (Y.-X. Ci, et al., Mikrochem. J., 52, 257–62 (1995)) are known and are explicitly considered to be within the scope of the meaning of peroxidase as used herein. Conjugates or complexes of a peroxidase and a biological molecule can also be used in the method for producing fluorescence, the only proviso being that the conjugate display peroxidase activity. Biological molecules which can be conjugated to one or more molecules of a peroxidase include DNA, RNA, oligonucleotides, antibodies, antibody fragments, antibody-DNA chimeras, antigens, haptens, proteins, lectins, avidin, streptavidin and biotin. Complexes including or incorporating a peroxidase such as liposomes, micelles, vesicles and polymers which are functionalized for attachment to biological molecules can also be used in the methods of the present invention.

Incorporation of certain enhancer compounds into the reaction mixture promotes the reactivity of the enzyme. Included among these enhancers are phenolic compounds and aromatic amines known to enhance other peroxidase reactions as described in U.S. Pat. No. 4,521,511 to Stout. Additional phenolic enhancers are disclosed in M. Ii, H. Yoshida, Y. Aramaki, H. Masuya, T. Hada, M. Terada, M. Hatanaka, Y. Ichimori, Biochem. *Biophys. Res. Comm.*, 193(2), 540–5 (1993), and in U.S. Pat. Nos. 5,171,668 and 5,206,149 which are incorporated herein by reference. Substituted and unsubstituted arylboronic acid compounds and their ester and anhydride derivatives as disclosed in U.S. Pat. No. 5,512,451 and incorporated herein by reference are also considered to be within the scope of enhancers useful in the present invention. Preferred enhancers include but are not limited to: p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol. Mixtures of more than one enhancer from those classes mentioned above can also be employed.

The use of nonionic surfactants as additives in the present fluorogenic reactions is advantageous. Incorporation of nonionic surfactants into reactions for producing fluorescence by the use of a peroxidase leads to an improvement in analytical sensitivity with respect to the peroxidase. Nonionic surfactants useful in the practice of the present invention include by way of example polyoxyethylenated alkylphenols, polyoxyethylenated alcohols, polyoxyethylenated ethers and polyoxyethylenated sorbitol esters.

Cationic surfactants, including quaternary ammonium salt compounds such as CTAB, are advantageous for use in increasing the level of fluorescence emitted when certain compounds of the present invention are reacted with a peroxidase and a peroxide.

Chelating agents which may be useful in the practice of the present invention include for example, polydentate cation complexing agents such as EDTA, EGTA and their salts as well as other reagents as are known in the art.

Organic solvents will be those which possess a high degree of water solubility and will typically comprise less than about 5% b volume of the formulation. Suitable organic solvents include the lower alcohols such as methanol, ethanol 2-propanol, ethylene glycol, propylene glycol and 2-methoxyethanol, low molecular weight ethers such as THF, dioxane, glyme and diglyme, acetone, DMF, acetamide and DMSO.

The reaction of the present invention is carried out in solution such as an aqueous buffer which may be in contact with the surface of a solid support such as a bead, tube, membrane or microwell plate coated with peroxidase. Suitable buffers include any of the commonly used buffers capable of maintaining a pH in the range of about 4 to about 10 for example, acetate, phosphate, borate, carbonate, tris, glycine, tricine, 2-amino-2-methyl-1-propanol and diethanolamine. The preferred method of practicing the invention in this regard is determined by the requirements of the particular intended use.

Light emitted by the present method can be detected by any suitable known means such as a spectrofluorimeter, x-ray film, high speed photographic film, a CCD camera, a scintillation counter, phosphor screens or visually. Each detection means has a different spectral sensitivity. The human eye is optimally sensitive to green light, CCD cameras display maximum sensitivity to red light, x-ray films with maximum response to either UV to blue light or green light are available. Choice of the detection device will be governed by the application and considerations of cost, convenience, and whether creation of a permanent record is required.

These and other advantages will be apparent by consideration of the examples.

EXAMPLES

Acridancarboxylic acid derivatives 1–11 were synthesized and tested in accordance with the methods of the present invention.

TABLE 1

Acridan Substrates Prepared.

| Compound | $R^1$ | $R^2$ | $R^3$–$R^{10}$ |
|---|---|---|---|
| 1 | $CO_2C_2H_5$ | $CH_3$ | all H |
| 2 | $CONHNH_2$ | $CH_3$ | all H |
| 3 | $4$-$CH_3OC_6H_4$ | $CH_3$ | all H |
| 4 | H | $4$-$FC_6H_4$ | all H |
| 5 | H | $CH_2C_6H_5$ | all H |
| 6 | H | $C_6H_5$ | $R^5$=$OCH_3$ |
| 7 | $CH_3$ | $CH_3$ | all H |
| 8 | COOH | $CH_2C_6H_5$ | all H |
| 9 | COOH | $CH_3$ | all H |
| 10 | H | $CH_3$ | all H |
| 11 | N-phenylacridanyl | $C_6H_5$ | all H |

Example 1

Synthesis of Peroxidase Substrate Compound 1

Compound 1 was prepared starting from commercially available acridine-9-carboxylic acid according to the sequence of conversion to the acid chloride using $SOCl_2$, esterification with ethanol, N-methylation with methyl triflate and reduction with zinc/acetic acid as is described in the literature. Alternately, it can be formed from Compound 9, the corresponding carboxylic acid by standard esterification conditions.

Example 2

Synthesis of Peroxidase Substrate Compound 2

Methyl N-methylacridan-9-carboxylate (0.728 g, 2.8 mmol) was dissolved in a solution of 25 mL of methanol and 2 mL of $CH_2Cl_2$. Hydrazine (1.9 mL, 62 mmol) was added and the reaction mixture refluxed for 1 day. The precipitate was collected, washed sequentially with methanol and $CH_2Cl_2$ and then recrystallized from $CH_2Cl_2$/hexane. $^1H$ NMR: ($CDCl_3$) $\partial$ 3.39 (s, 3H), 3.69 (d, 2H), 4.85 (s, 1H), 6.65 (br s, 1H), 6.96–7.35 (m, 8H).

Example 3

Synthesis of Peroxidase Substrate Compound 3

N-methylacridinium triflate (1.0 g, 2.9 mmol) was suspended in 30 mL of THF and cooled to 0° C. under a blanket of argon. A solution of 4-methoxyphenylmagnesium bromide in THF (7 mL of 0.5 M) was injected by syringe and the mixture stirred for 3 h. The solvent was evaporated and the residue chromatographed on silica with 10–20% EtOAc/hexane. Compound 3 was obtained as a white solid, 818 mg. $^1H$ NMR: ($CDCl_3$) $\partial$ 3.41 (s, 3H), 3.73 (3, 3H), 5.13 (s, 1H), 6.74–7.23 (m, 12H).

Example 4

Synthesis of Peroxidase Substrate Compound 4

1.0 g of acridan ($5.5 \times 10^{-3}$ mol), 24.8 mg of palladium acetate ($1.1 \times 10^{-4}$ mol), 17.8 mg of tri-t-butylphosphine ($8.8 \times 10^{-5}$ mol), 795 mg of sodium t-butoxide ($8.29 \times 10^{-3}$ mol), and 1.06 g of 1-bromo-4-fluorobenzene ($6.0 \times 10^{-3}$ mol) were placed in a round bottom flask and the flask was purged with argon. Anhydrous toluene (10 mL) was added to the flask and the black solution was allowed to stir at room temperature for 16 h.

9.0 g of acridan ($4.96 \times 10^{-2}$ mol), 446 mg of palladium acetate ($1.98 \times 10^{-3}$ mol), 321 mg of tri-tert-butylphosphine ($1.58 \times 10^{-9}$ mol), 7.16 g of sodium tert-butoxide ($7.4 \times 10^{-2}$ mol), and 9.6 g of 1-bromo-4-fluorobenzene (0.054 mol) were placed in a round bottom flask and the flask was purged with argon. 90 ml of anhydrous toluene was added to the flask and the black solution was allowed to stir at room temperature for 2 hours.

The combined reaction mixtures described above were filtered through a Buchner funnel and washed with methylene chloride. The filtrate was then concentrated in vacuo and the residue was taken up in methylene chloride and refiltered. Tlc analysis showed that only the filtrate contained product. 50 g of silica gel was added to the filtrate and this solution was concentrated to dryness and then loaded on top of a column of silica gel in 5% ethyl acetate in hexanes. The column was eluted with 5% ethyl acetate in hexanes, but the product began to precipitate on the column, so the column was eluted with neat $CH_2Cl_2$. Two fractions of product were collected and concentrated to dryness, and $^1H$ NMR showed both fractions contained pure product. The two fractions are combined to afford 14 g of the desired product. $^1H$ NMR: ($CDCl_3$) $\partial$ 4.22 (s, 2H), 6.16–6.19 (d, 2H), 6.84–6.88 (t, 2H), 6.93–6.98 (t, 2H), 7.13–7.16, (d, 2H), 7.29–7.31 (d, 4H).

Example 5

Synthesis of Peroxidase Substrate Compound 5

A 3-L flask was charged with 200 g of acridone (1.03 mol), 49.3 g of 60% NaH/oil dispersion (1.23 mol) and 1 L of DMF. The mixture became warm and was stirred over night under argon. Benzyl bromide (185 g, 1.08 mol) was added to the brown solution. The reaction became warm as stirring was maintained. After 2 h the contents had nearly solidified. An hour later, 1 L of ether was added and the mixture suction filtered to remove the solid, washing with another 1 L of ether and then, carefully, with 3 L of water. A second crop was isolated by evaporating the combined filtrates to dryness yielding a yellow solid. This solid was washed with 1 L of water, air dried and then washed with 400 mL of acetone. The combined yield was 234 g, 80% of N-benzylacridone.

The N-benzylacridone (229 g, 0.8 mol) was reduced with 104.7 g of lithium aluminum hydride (2.76 mol) in 4 L of diethyl ether. The grey slurry was then purged with argon and the reaction warmed spontaneously to reflux. The mixture was stirred over night at room temperature. The mixture was quenched with 100 mL of water, followed by 100 mL of 15% aq. NaOH and 315 mL of water. The solid was suspended and washed thoroughly with 4 L of $CH_2Cl_2$. The filtrate was concentrated to dryness to afford 204 g of the acridan as a white solid (96%). $^1H$ NMR: ($CDCl_3$) $\partial$ 4.08 (s, 2H), 5.13 (s, 2H), 6.65–6.68 (d, 2H), 6.85–6.9 (t, 2H), 7.01–7.06 (t, 2H), 7.13–7.34 (m, 7H).

Example 6

Synthesis of Peroxidase Substrate Compound 6

Compound 6 was prepared as described in U.S. patent application Publication No. 2001/0031869, published on Oct. 18, 2001. The preparation of compound is described in connection with the synthesis of a compound designated 1p therein.

Example 7

Synthesis of Peroxidase Substrate Compound 7

N-Methylacridinium triflate (5.0 g, 14.5 mmol), prepared by alkylation of acridine with methyl triflate, was suspended in 100 mL of dry THF under argon and treated with 5.8 mL of 3 M methylmagnesium bromide (17 mmol) in hexanes by stirring over night. The solution was concentrated to dryness. The product was isolated after chromatographic purification on a silica gel column eluted with 5% EtOAc/hexanes. There was obtained 2.82 g (92.5%) of the 9-methylated derivative as a white solid. $^1H$ NMR: ($CDCl_3$) $\partial$ 1.31–1.33 (d, 3H), 3.39 (s, 3H), 3.94–4.02 (q, 1H), 6.89–6.97 (m, 4H), 7.17–7.23 (m,4H).

Example 8

Synthesis of Peroxidase Substrate Compound 8

A solution of Compound 5, N-benzylacridan (10 g, 37 mmol) in 200 mL of dry THF under inert atmosphere was cooled to 78° C. and 25.0 mL of 2.5 M n-butyllithium in hexanes (37.5 mmol) was added dropwise over 15 min. The solution was stirred at –78° C. for 1 h and then warmed to room temperature over 45 min. The reaction mixture was again cooled to –78° C. and ca. 200 g of crushed dry ice was added causing a precipitate to form. The reaction was allowed to slowly warm to room temperature and stirring under argon was continued over night. The mixture was evaporated, the solid was then suspended in 300 mL of water and acidified to pH 3 with 12N HCl. The solid was collected, washed with water, dissolved in $CH_2Cl_2$, dried over sodium sulfate and concentrated to afford 11 g of N-benzyl-acridan-9-carboxylic acid. $^1H$ NMR: ($CDCl_3$) $\partial$ 4.99 (s, 1H), 5.12 (s, 2H), 6.72–6.75 (d, 2H), 6.88–6.94 (t, 2H), 7.10–7.17 (m, 4H), 7.22–7.32 (m, 5H).

Example 9

Synthesis of Peroxidase Substrate Compound 9

Carboxylation of 49.6 g (25.5 mmol) of Compound 10 by treatment with n-BuLi in THF followed by addition of crushed dry ice, as described in Example 8, yielded 55.5 g (91%) of carboxylic acid 9. $^1$H NMR: (DMSO-d$_6$) ∂ 3.33 (s, 3H), 4.93 (s, 1H), 6.91–7.26 (m, 8H).

Example 10

Synthesis of Peroxidase Substrate Compound 10

Commercially available N-methylacridone 60.2 g was reduced with LiAlH$_4$ in diethyl ether as described in Example 5. The yield was 49.6 g, 88%. $^1$H NMR: (CDCl$_3$) ∂ 3.38 (s, 3H), 3.89 (s, 3H), 6.87–7.22 (m, 8H).

Example 11

Synthesis of Peroxidase Substrate Compound 11

Acridine (5.2 g, 29 mmol) was dissolved in 200 mL of CH$_2$Cl$_2$ and placed under argon. Zinc dust (2.09 g, 32 mmol) and 1.9 mL of acetic acid (33 mmol) were added and the mixture stirred for two days. The solid was collected by filtration and washed with CH$_2$Cl$_2$. After air drying the solid was ground to a fine powder and stirred 30 min with 300 mL of 2N HCl. The solid was again filtered off and washed sequentially with water, 2-propanol and hexane. After drying there resulted 4.71 g of 9,9'-biacridanyl (90%).

9,9'-Biacridanyl (1.0 g, 27.7 mmol), 62.2 mg of palladium acetate (0.27 mmol), 45 mg of tri-tert-butylphosphine (0.22 mmol), 0.80 g of sodium tert-butoxide (3 equiv.), and 0.96 g of bromobenzene (6.1 mmol) were placed in a round bottom flask and the flask was purged with argon. Dry toluene (30 mL) was added to the flask and the black solution was allowed to stir at room temperature over night. The reaction mixture was poured into 100 mL of CH$_2$Cl$_2$ and filtered through 20 g of silica, washing with additional CH$_2$Cl$_2$. Evaporation of the solvent left a yellow solid which was chromatographed on silica with 10% EtOAc/hexane. Compound 11 (1.25 g, 88%) was obtained as a pale yellow solid. $^1$H NMR: (CDCl$_3$) ∂ 4.41 (s, 2H), 5.99–6.02 (d, 4H), 6.66–6.78 (m, 12H), 6.94–7.0 (m, 4H), 7.35–7.48 (m, 6H).

Example 12

Preparation of Reagent Formulations

Enhanced reagent formulations containing each of Compounds 1–13 were prepared in either the Basic Formulation or the Acidic Formulation described below.

| Basic Formulation | Acidic Formulation |
|---|---|
| 10 mM Tris buffer, pH 8 | 10 mM Na acetate buffer, pH 5 |
| 0.05 mM substrate | 0.05 mM substrate |
| 0.5 mM urea peroxide | 0.5 mM urea peroxide |
| 1 mM EDTA | 1 mM EDTA |
| 0.1 mM p-phenylphenol | 0.1 mM p-phenylphenol |
| 0.025% Tween-20 | 0.025% Tween-20 |

Example 13

Fluorescence Spectra

Fluorescence spectra were obtained on a Jobin Yvon/SPEX FluoroMax-3 spectrofluorometer with the excitation and emission slits set at 1.0 nm bandpass. UV Fluorimeter cuvettes (3.5 mL capacity, Perfector Scientific) were used.

Example 14

Evaluation of Substrates

Each of Compounds 1–13 was tested for production of a fluorescent product by reaction with HRP followed by spectrofluorometric analysis. A representative procedure using Compound 1 is described below. Essentially the same procedure was used for the other compounds.

Three mL of a 0.05 mM solution of ethyl N-methylacridan 9-carboxylate (Compound 1) in the acidic formulation were pipetted into a cuvette. Excitation (λem=524 nm) and emission (λex=364 nm) spectra were recorded. HRP (13.8 fmol, 4.6×10$^{-12}$M) was added and mixed thoroughly. The increase in fluorescence at 524 nm was recorded over 15 min. Excitation (λem=524 nm) and emission (λex=357 nm) spectra were recorded again.

TABLE 2

Fluorescent Properties of Acridan Substrates.

| Compound | pH 5 | pH 8 |
|---|---|---|
| 1 | 524 | 524 |
| 2 | 487 | 488 |
| 3 | 484 | 484 |
| 4 | 497 | 496 |
| 5 | 494 | 494 |
| 6 | 512 | 511 |
| 7 | 490 | 488 |
| 8 |  | 493 |
| 9 |  | 489 |
| 10 |  | 490 |
| 11 | 494 | 494 |

Example 15

Fluorescence Signal/Background Measurements

Three mL of a solution of each substrate in either the acidic or basic formulation described in Example 12 were pipetted into a cuvette. HRP (13.8 fmol, 4.6×10$^{-12}$M) was added and mixed thoroughly. The increase in fluorescence at the maximum was recorded after 15 min for each substrate. Signal-background values were calculated by comparing the fluorescence intensities at t=0 minutes and t=15 minutes.

TABLE 3

Fluorescent Intensity of Acridan Substrates in the Presence of HRP (as S/B).

| Compound | pH 5 | pH 8 |
|---|---|---|
| 1 | 29.5 | 11.0 |
| 2 | 6.6 |  |
| 3 | 1.4 |  |
| 4 | 3.9 |  |
| 5 | 5.6 |  |
| 6 | 3.6 |  |
| 7 | 15.8 |  |
| 9 |  | 4.3 |
| 11 | 84.0 | 6.1 |

Example 16

Figure 1:
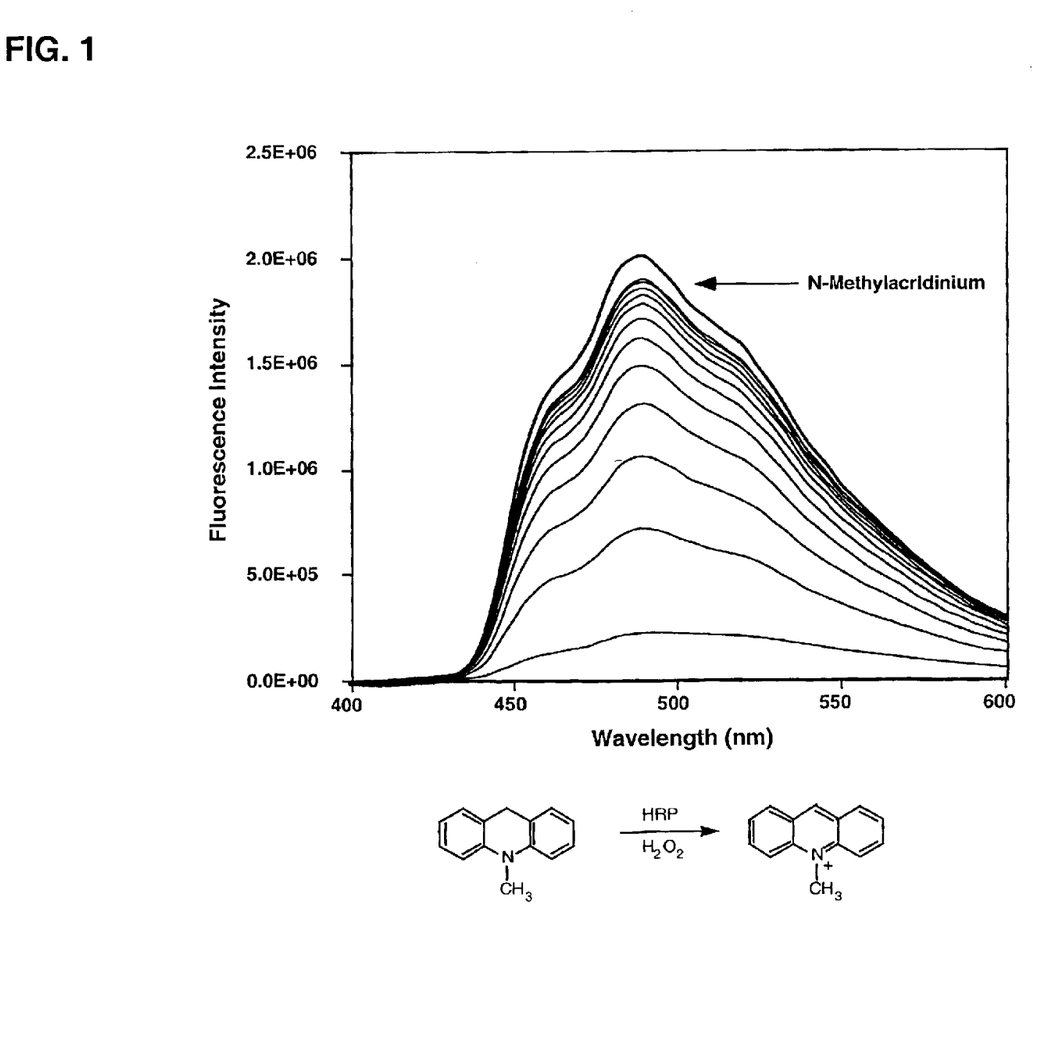
FIG. 1 is a graph showing a series of sequential fluorescence spectra obtained from a reaction solution containing Compound 10 and HRP. The spectra correspond to the fluorescence of the acridinium product. For comparison, the fluorescence spectrum of an independently prepared sample of N-methylacridinium triflate is shown.

Fluorescence Spectra of the Reaction Product of N-Methylacridan (Compound 10) and HRP Three mL of a 0.05 mM solution of N-methylacridan in the acidic formulation were pipetted into a cuvette. HRP (13.8 fmol, 4.6×10$^{-12}$M) was added and mixed thoroughly. Emission spectra (excitation at 357 nm) were obtained at 4.5 minute intervals over 1.8 h. The set of emission spectra obtained are shown in FIG. 1. The emission spectrum (excitation at 357 nm) of a 0.05 mM solution of N-methyl acridinium triflate in the acidic formulation is also shown for comparison with the emission spectra from the N-methylacridan/HRP solution. The identity of the spectra demonstrates enzymatic conversion of Compound 10 to the fluorescent acridinium compound.

Example 17

Kinetics of Fluorescent Product Formation from Compound 10

Figure 2:
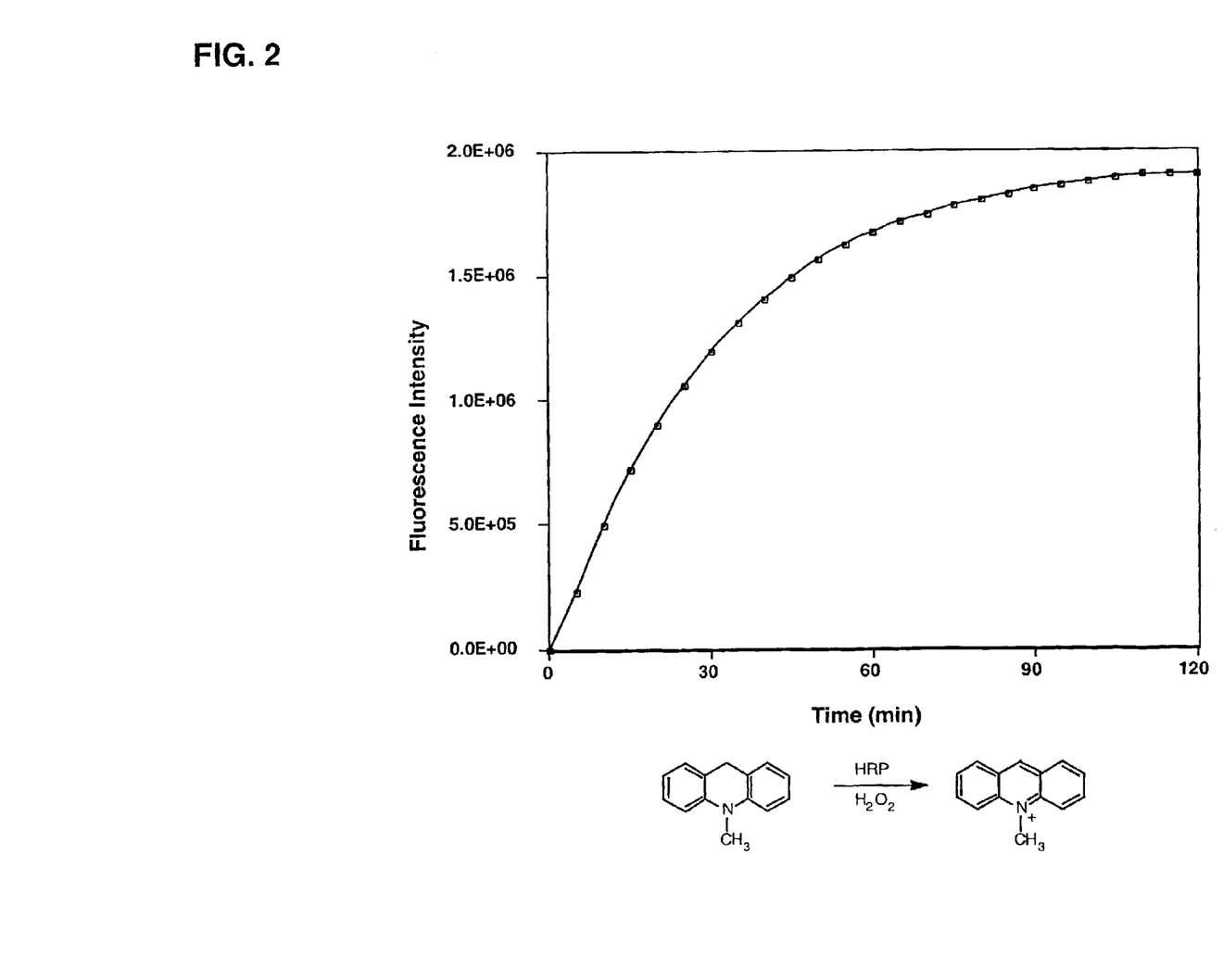
FIG. 2 is a graph showing the time course of the generation of fluorescent product from the reaction described in FIG. 1. The product is monitored by excitation at 357 nm and detecting fluorescence emission at 495 nm.

FIG. 2 depicts the fluorescence intensity at 495 nm (with excitation at 357 nm) from the reaction solution of Example 16 as a function of time. Fluorescence intensity reached a maximum in 2 h and remained constant.

Example 18

Fluorescent Detection Sensitivity of HRP Using Compound 1

Figure 3:
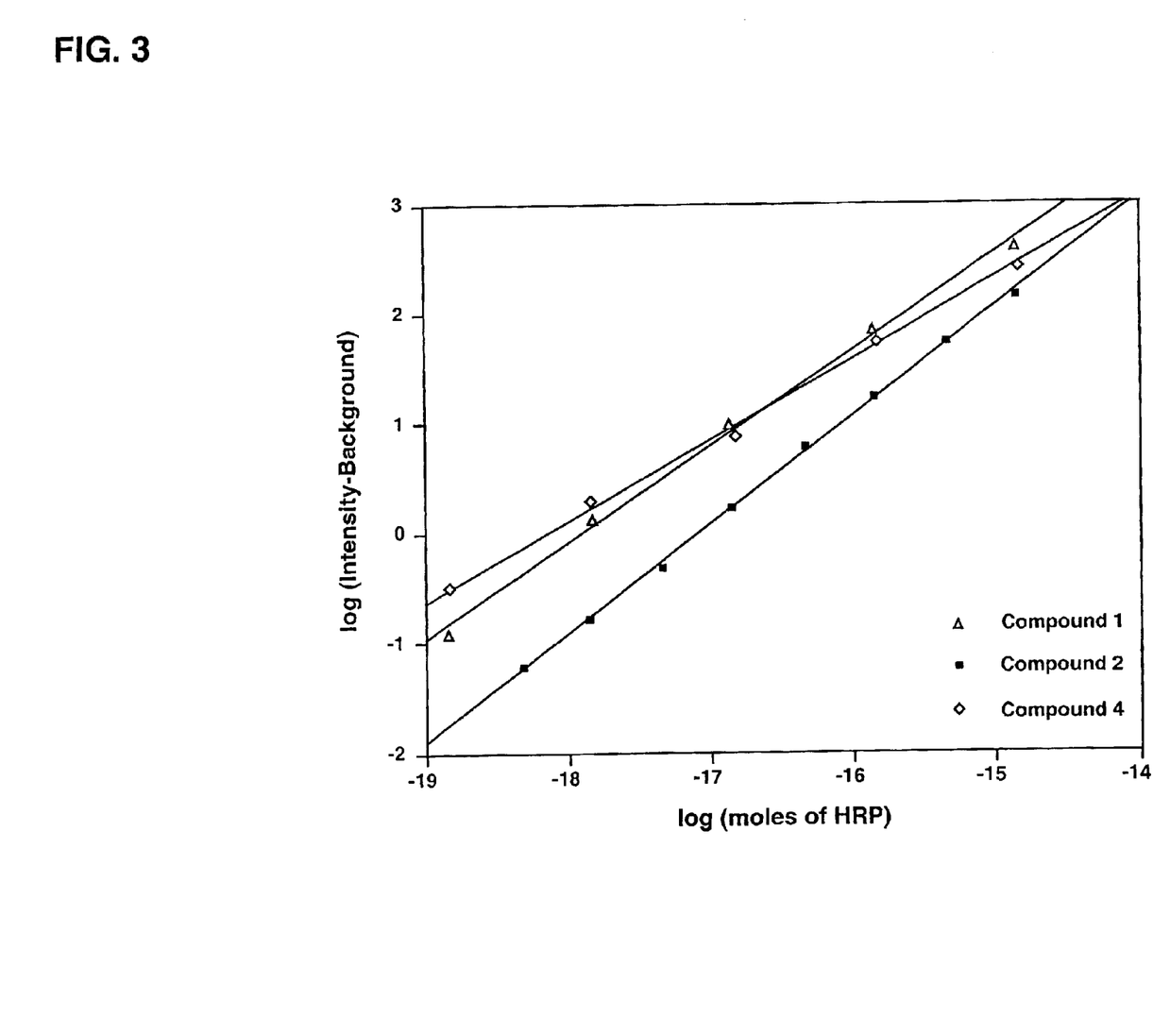

Fluorescence detection limits were obtained on a Labsystems Fluoroskan Ascent microtiter plate fluorometer using an excitation bandpass filter (380 nm) and an emission bandpass filter (465 or 530 nm). Black MicroFLUOR B 12-well strips (Dynatech Laboratories) were used. HRP was serially diluted in type 1 water and 10 µl of diluted HRP was pipetted into each well. A 0.05 mM solution of ethyl N-methylacridan 9-carboxylate in the acidic formulation was prepared and 100 µL pipetted into each well. The strips were then read on the Fluoroskan Ascent with the 380 nm-530 nm filter set. FIG. 3 demonstrates the excellent sensitivity obtained with this substrate.

Example 19

Fluorescent Detection Sensitivity of HRP Using Compound 2

HRP was serially diluted in type 1 water and 10 µl of diluted HRP was pipetted into each well. A 0.05 mM solution of N-methyl acridan 9-carboxylic acid hydrazide in the basic formulation was prepared and 100 µl pipetted into each well. The strips were then read on the Fluoroskan Ascent with the 380 nm–465 nm filter set. FIG. 3 demonstrates the excellent sensitivity obtained with this substrate.

Example 20

Fluorescent Detection Sensitivity of HRP Using Compound 4

HRP was serially diluted in type 1 water and 10 µl of diluted HRP was pipetted into each well. A 0.05 mM solution of N-(4-fluorophenyl)acridan in the acidic formulation was prepared and 100 µl pipetted into each well. The strips were then read on the Fluoroskan Ascent with the 380 nm–465 nm filter set. FIG. 3 demonstrates the excellent sensitivity obtained with this substrate.

Example 21

Kinetics of Fluorescent Product Formation from Compound 12

Figure 4:
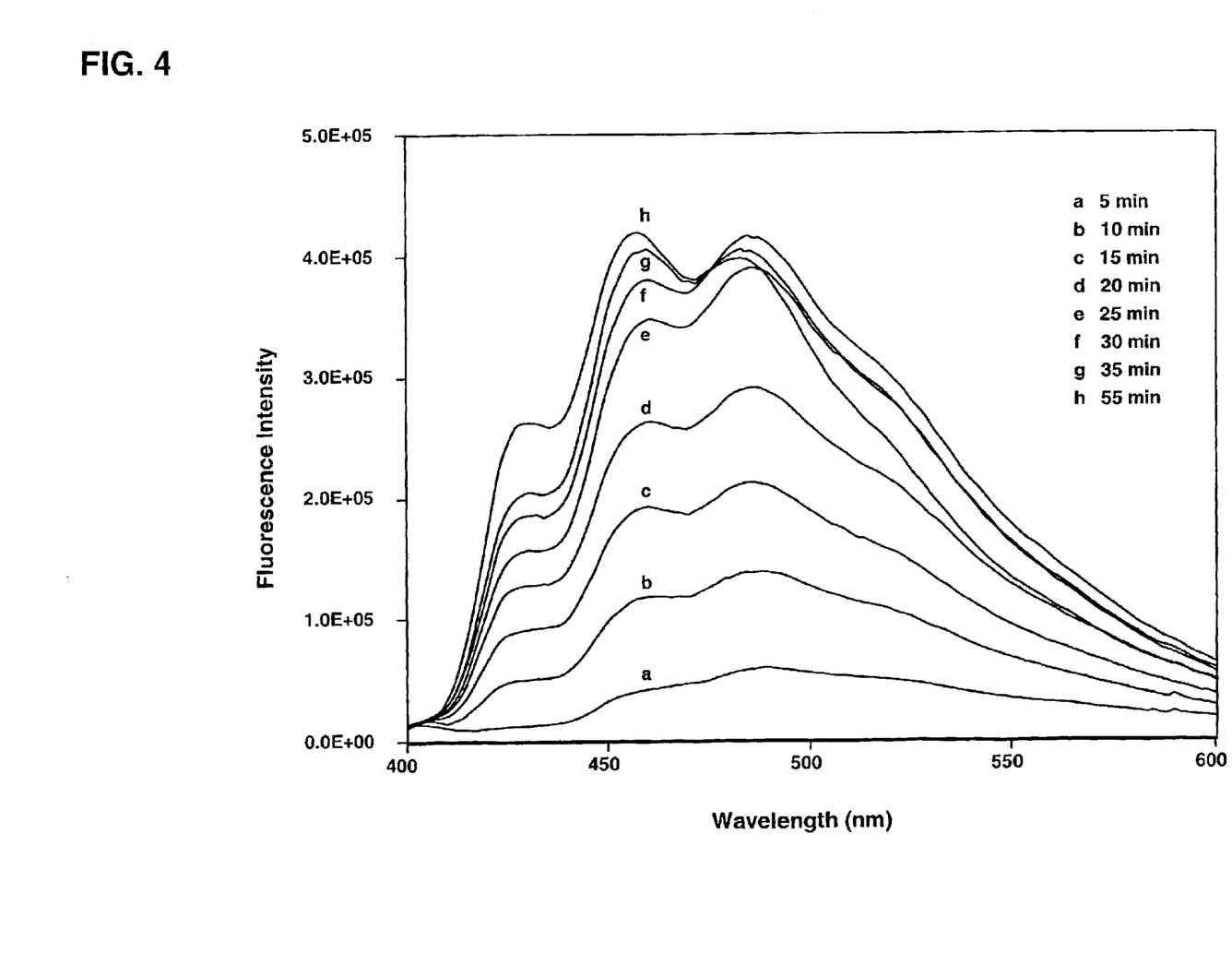
FIG. 4 is a graph showing the a series of sequential fluorescence spectra obtained from a reaction solution containing compound 12 and HRP. The spectra reveal the formation of the acridinium ester intermediate and N-methylacridone product.

Three mL of a reagent containing 0.3 mM 2',3',6'-trifluorophenyl 10-methylacridan-9-carboxylate (compound 12), 0.1 mM 4-phenylphenol, 0.5 mM urea peroxide, 1 mM EDTA, and 0.025% TWEEN 20 in 0.01 M tris buffer, pH 8.0 were pipetted into a cuvette. HRP (13.8 fmol, $4.6 \times 10^{-12}$M) was added and mixed thoroughly. Emission spectra (excitation at 357 nm) were obtained at 4.5 minute intervals over 1.8 h. The set of emission spectra obtained are shown in FIG. 4. The spectra depict the progression of the reaction showing the grow in of acridinium fluorescence and gradual predominance of N-methylacridone fluorescence.

Example 22

Detection of HRP with Acridan Substrate 13 by Chemiluminescence

Chemiluminescent HRP detection limit using a reagent composition containing 0.05 mM 2',3',6'-trifluorophenyl 3-methoxy-10-methylacridan-9-carboxylate (compound 13), 0.1 mM 4-phenylphenol, 0.5 mM urea peroxide, 1 mM EDTA, and 0.025% TWEEN 20 in 0.01 M tris buffer, pH 8.0 was obtained on a Labsystems Luminoskan microtiter plate reader. White Microlite 1 FB 12-well strips (Dynatech Laboratories) containing 100 µL of the reagent in each well were reacted with 10 µL of HRP dilutions. Light intensity was measured at 10 min.

Example 23

Detection of HRP with Acridan Substrate 13 by Fluorescence

Figure 5:
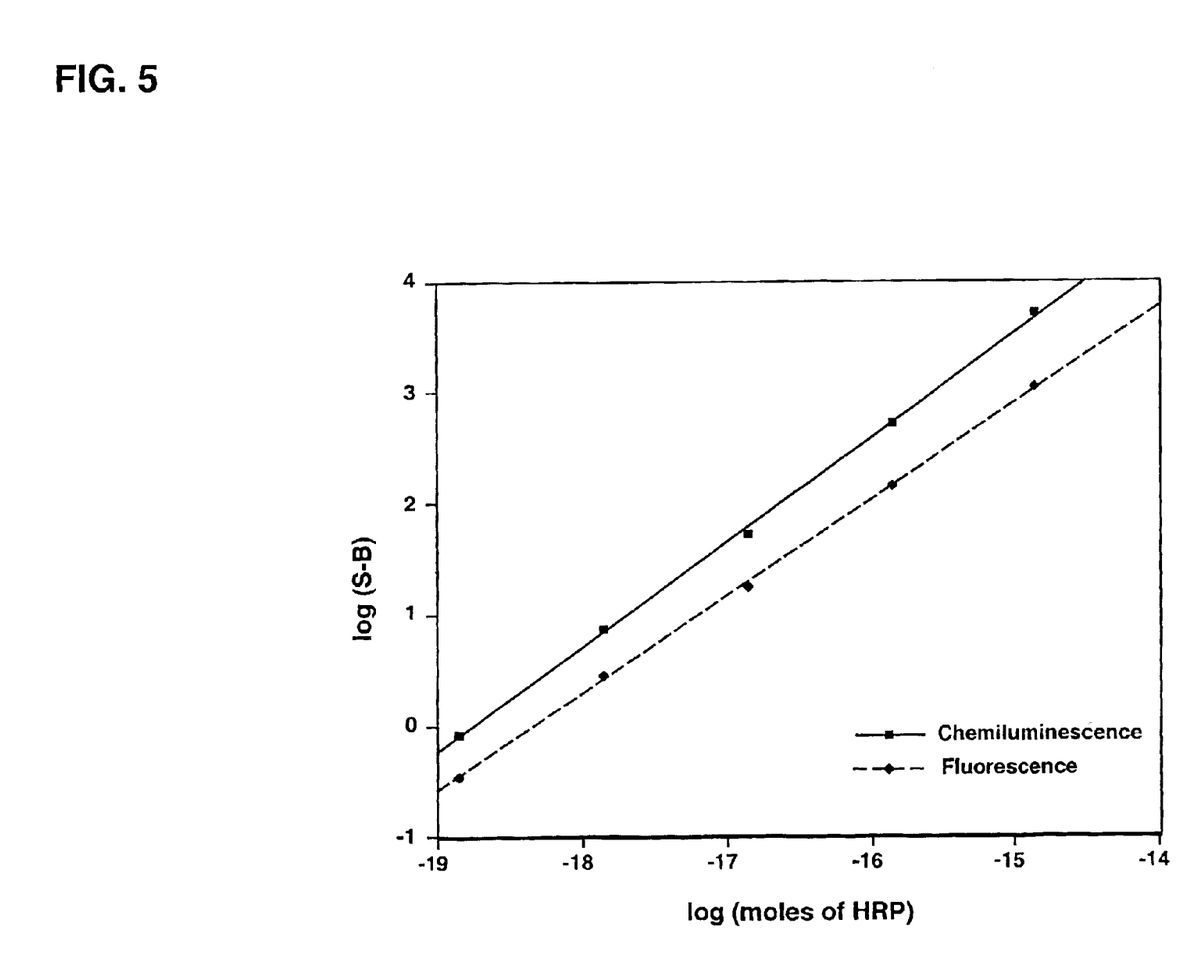
FIG. 5 is a graph showing the linearity of detection of HRP using reagent compositions containing substrate 13 with fluorescence and chemiluminescence detection. A solution containing 0.05 mM compound 13, 0.1 mM 4-phenylphenol, 0.5 mM urea peroxide, 1 mM EDTA, 0.025% TWEEN 20 in 10 mM tris, pH 8.0 was reacted with the indicated quantities of HRP. Chemiluminescence intensity was measured 10 min after addition of enzyme, fluorescence at 515 nm was measured 30 min after addition of enzyme.

Sensitive detection of HRP was achieved using the reaction solutions of Example 22 producing fluorescence by the second mode. After making the chemiluminescence measurement, the strips were transferred to the fluorometer and fluorescence intensity determined at 530 nm with excitation at 380 nm. FIG. 5 shows that the method was able to detect less than 1 amol of HRP. The sensitivity was equivalent to chemiluminescent detection with the same substrate.

Example 24

Fluorescent Detection of HRP Using Compound 14

Forty µL of a detection reagent consisting of 0.05 mM compound 14, 0.6 mM urea peroxide, 0.1 mM p-phenylphenol, 0.025% TWEEN 20, 1 mM EDTA in 0.01 M tris buffer, pH 8.0 was reacted with 1 µL of HRP ($1.4 \times 10^{-16}$ mol) at room temperature. Acridinium ester end product formation was detected after 5 min and continued to increase over 1 h as detected by spectrophotometry and fluorescence at 500 nm.

14

In a similar experiment with the substrate 2,3,6-trifluorophenyl 1,6-dimethoxy-4,10-dimethylacridan-9-carboxylate (Compound 15), reaction with HRP resulted in fluorescent acridinium end product formation which was detectable by spectrophotometry and fluorescence at 500 nm.

We claim:
1. A method for producing fluorescence comprising
   a) providing a peroxidase and a fluorogenic substrate having the formula wherein $R^1$ is a group selected to be inert to attack by peroxide and containing from 1 to 20 atoms selected from C, H, N, O, S, P, Si and halogens, $R^2$ is selected from alkyl, substituted alkyl, aryl substituted aryl, aralkyl and substituted aralkyl groups, and $R^3$ to $R^{10}$ are each groups containing from 1 to 20 atoms selected from C, H, N, O, S, P, Si and halogens;
   b) reacting the peroxidase with the fluorogenic substrate to produce a fluorescent product which accumulates in the reaction and undergoes no further reaction; and
   c) irradiating the fluorescent product at a suitable wavelength of light to cause the fluorescent product to emit fluorescence.

2. The method of claim 1 with the proviso that $R^1$ does not comprise an aryl ester (—COOAr), an alkyl ester (—COOR) wherein the alkyl group R is substituted with electron-withdrawing groups selected from halogen, cyano and nitro groups, an alkyl thioester (—COSR), an aryl thioester (—COSAr), a sulfonimide (—CO(NR)SO$_2$R'), an acyl halide group —C(=O)X wherein X is a halogen or a cyano group.

3. The method of claim 1 wherein $R^1$ is selected from alkyl, substituted alkyl, alkenyl, substituted alkenyl, alkynyl, substituted alkynyl, alkoxy, alkylthio, aryl, substituted aryl, aralkyl, substituted aralkyl, carboxylic acid, carboxylate salt, carboxamide, alkyl carboxyl ester, carboxyl hydrazide groups, keto groups, —CHO, amino, alkylamino, arylamino, and a hydrogen atom.

4. The method of claim 1 wherein the groups $R^3$ to $R^{10}$ are independently selected from hydrogen, alkyl, alkoxy, alkylthio, amino, alkylamino, arylamino, aryl, alkenyl, alkynyl, halogen, hydroxy, mercapto, sulfonate, sulfate, and phosphate.

5. The method of claim 1 wherein each of the groups $R^3$ to $R^{10}$ is hydrogen.

6. The method of claim 1 wherein the compound of formula I contains at least one group which imparts water solubility.

7. The method of claim 6 wherein the group which imparts water solubility is selected from carboxylate, sulfonate, sulfate, phosphate, ammonium and phosphonium groups.

8. The method of claim 1 wherein the compound of formula I is selected from the group of compounds 1–11 having the structures below

1

2

3

4

5

6

9. The method of claim 1 further comprising providing peroxide for reacting with the peroxidase.

10. The method of claim 1 wherein the peroxide is produced by the reaction of an oxidase enzyme with an oxidase substrate.

11. The use of the method of claim 1 in an assay of the peroxidase enzyme comprising the further steps of:
   d) detecting the fluorescence emitted by the fluorescent product; and
   e) relating the amount of fluorescence produced to the amount of the peroxidase.

12. The method of claim 11 wherein the peroxidase enzyme is conjugated to a biological molecule.

13. The use of the method of claim 1 in an assay of an analyte comprising the further steps of:
   d) detecting the fluorescence emitted by the fluorescent product;
   e) relating the amount of fluorescence produced to the amount of the peroxidase; and
   f) relating the amount of the peroxidase to the amount of the analyte.

14. The method of claim 1 wherein the fluorogenic substrate is provided as a reagent composition comprising the substrate, a peroxide and an enhancer.

15. The method of claim 14 wherein the enhancer selected from phenols, aromatic amines, arylboronic acids and arylboronic acid esters.

16. The method of claim 14 wherein the enhancer is selected from p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol.

* * * * *